US00PP16800P2

(12) United States Plant Patent
Vlielander

(10) Patent No.: US PP16,800 P2
(45) Date of Patent: *Jul. 11, 2006

(54) *KALANCHOE* PLANT NAMED 'CHER'

(50) Latin Name: *Kalanchoe blossfeldiana*
Varietal Denomination: Cher

(75) Inventor: Ike Vlielander, De Lier (NL)

(73) Assignee: Fides Goldstock Breeding B.V., Maasland (NL)

( * ) Notice: Subject to any disclaimer, the term of this patent is extended or adjusted under 35 U.S.C. 154(b) by 14 days.

This patent is subject to a terminal disclaimer.

(21) Appl. No.: 11/021,995

(22) Filed: Dec. 24, 2004

(51) Int. Cl.
*A01H 5/00* (2006.01)

(52) U.S. Cl. ..... Plt./339
(58) Field of Classification Search ..... Plt./335, Plt./339
See application file for complete search history.

(56) References Cited

U.S. PATENT DOCUMENTS

PP4,343 P * 12/1978 Hope ..... Plt./339
PP10,454 P * 6/1998 Vlielander ..... Plt./335
PP13,365 P2 * 12/2002 Vlielander ..... Plt./341
PP14,712 P2 * 4/2004 Vlielander ..... Plt./339

OTHER PUBLICATIONS

UPOV ROM GTITM Computer Database, GTI Jouve Retrieval Software 2005/02 Citation for 'Cher'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Kalanchoe* plant named 'Cher', characterized by its numerous multi-petalled red purple-colored flowers; upright, uniform and compact plant habit; freely branching growth habit; medium green-colored glossy leaves; and excellent postproduction longevity.

1 Drawing Sheet

Botanical designation: *Kalanchoe blossfeldiana.*
Cultivar denomination: 'Cher'.

BACKGROUND OF THE INVENTION

The present invention relates to a new and distinct cultivar of *Kalanchoe* plant, botanically known as *Kalanchoe blossfeldiana,* and hereinafter referred to by the name 'Cher'.

The new *Kalanchoe* is a product of a planned breeding program conducted by the Inventor in De Lier, The Netherlands. The objective of the breeding program is to create new *Kalanchoes* with multi-petalled flowers.

The new *Kalanchoe* originated from a cross-pollination made by the Inventor in September, 1999, of the *Kalanchoe* cultivar Leonardo, disclosed in U.S. Plant Pat. No. 13,365, as the female, or seed, parent with the *Kalanchoe* cultivar Klabat, disclosed in U.S. Plant Pat. No. 10,454, as the male, or pollen, parent. The new *Kalanchoe* was selected by the Inventor in 2000 in a controlled environment in De Lier, The Netherlands as a single flowering plant from the resultant progeny of the cross-pollination on the basis of its multi-petalled flowers.

Asexual reproduction of the new *Kalanchoe* by terminal vegetative cuttings taken at De Lier, The Netherlands, since 2000 has shown that the unique features of this new *Kalanchoe* are stable and reproduced true to type in successive generations.

BRIEF SUMMARY OF THE INVENTION

The cultivar Cher has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Cher'. These characteristics in combination distinguish 'Cher' as a new and distinct cultivar:

1. Numerous multi-petalled red purple-colored flowers.
2. Upright, uniform and compact plant habit.
3. Freely branching growth habit.
4. Medium green-colored glossy leaves.
5. Excellent postproduction longevity.

Plants of the new *Kalanchoe* can be compared to plants of the female parent, the cultivar Leonardo. In side-by-side comparisons conducted in De Lier, The Netherlands, plants of the new *Kalanchoe* differed from plants of the cultivar Leonardo primarily in flower color as plants of the new *Kalanchoe* have darker-colored flowers than plants of the cultivar Leonardo.

Plants of the new *Kalanchoe* can be compared to plants of the male parent, the cultivar Klabat. In side-by-side comparisons conducted in De Lier, The Netherlands, plants of the new *Kalanchoe* differed from plants of the cultivar Klabat in the following characteristics:

1. Plants of the new *Kalanchoe* were more compact than plants of the cultivar Klabat.
2. Plants of the new *Kalanchoe* had multi-petalled flowers whereas plants of the cultivar Klabat had four petals per flower.
3. Flower petals of plants of the new *Kalanchoe* were red purple in color whereas flower petals of plants of the cultivar Klabat were orange and yellow-bicolored.

Plants of the new *Kalanchoe* can also be compared to plants of the *Kalanchoe* cultivar La Douce, disclosed in U.S. Plant Pat. No. 14,712. In side-by-side comparisons conducted in De Lier, The Netherlands, plants of the new *Kalanchoe* differed from plants of the cultivar La Douce in the following characteristics:

1. Plants of the new *Kalanchoe* had larger flowers than plants of the cultivar La Douce.
2. Flower color of plants of the new *Kalanchoe* was darker than flower color of plants of the cultivar La Douce.

BRIEF DESCRIPTION OF THE PHOTOGRAPH

The accompanying colored photograph illustrates the overall appearance of the new *Kalanchoe,* showing the colors as true as it is reasonably possible to obtain in colored reproductions of this type. Colors in the photograph may differ slightly from the color values cited in the detailed botanical description which accurately describe the colors of the new *Kalanchoe.* The photograph comprises a side perspective view of a typical plant of 'Cher' grown in a container.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photograph and for the description were grown during the autumn in De Lier, The Netherlands, in a glass-covered greenhouse. During the production of the plants, day temperatures ranged from 20° C. to 25° C.; night temperatures ranged from 19° C. to 21° C.; and light levels ranged from 10,000 to 50,000 lux. Unrooted cuttings were directly stuck in 10-cm containers and received long day/short night conditions (more than 14 hours of light) for about three weeks; plants then received photoinductive short day/long night conditions (minimum 14 hours darkness) until flowering. Plants were about 15 weeks old from an unrooted cutting when the photograph and the description were taken.

Botanical classification: *Kalanchoe blossfeldiana* cultivar Cher.

Parentage:

*Female, or seed, parent.*—*Kalanchoe blossfeldiana* cultivar Leonardo, disclosed in U.S. Plant Pat. No. 13,365.

*Male, or pollen, parent.*—*Kalanchoe blossfeldiana* cultivar Klabat, disclosed in U.S. Plant Pat. No. 10,454.

Propagation:

*Type cutting.*—Terminal vegetative cuttings.

*Time to initiate roots.*—Summer: About 10 days at 21° C. Winter: About 14 days at 21° C.

*Time to produce a rooted cutting.*—Summer: About 21 days at 21° C. Winter: About 28 days at 21° C.

*Root description.*—Numerous; fine; fibrous; greyed white in color.

*Rooting habit.*—Freely branching.

Plant description:

*Form.*—Upright, uniform and compact plant habit. Very freely flowering with numerous compound cymes. Inverted triangle with rounded crown. Appropriate for 10-cm to 15-cm containers.

*Crop time.*—About 14 to 17 weeks: three to five weeks under long day/short night conditions followed by 11 to 13 weeks of short day/long night conditions. Moderately vigorous.

*Plant height at flowering.*—About 17 cm.

*Plant diameter at flowering.*—About 15 cm.

*Branching habit.*—Freely branching; typically seven to eight lateral branches develop per plant. Pinching (removal of terminal apex) is not required but will enhance lateral branch development.

*Lateral branch description.*—Length: About 10 cm to 14 cm. Diameter: About 2 cm to 5 cm. Internode length: About 2 cm to 3 cm. Aspect: Erect. Strength: Strong. Texture: Smooth, glabrous. Color: 138A.

*Foliage description.*—Leaves simple, opposite, generally symmetrical. Quantity per plant: About 8 to 13 mature leaves and 14 to 22 generative leaves. Length: About 10.5 cm. Width: About 6.5 cm. Shape: Ovate to elliptical. Apex: Obtuse. Base: Obtuse. Margin: Crenate. Texture, upper and lower surfaces: Leathery, smooth, glabrous and succulent. Color: Developing and fully expanded leaves, upper surface: 138A; glossy. Developing and fully expanded leaves, lower surface: 138B. Venation, upper surface: 138A. Venation, lower surface: 138B. Petiole length: About 1.5 cm. Petiole diameter: About 4 mm to 7 mm. Petiole color, upper and lower surfaces: 138A to 138B.

Flower description:

*Flower type and habit.*—Multi-petalled flowers arranged in compound dichasial cymes that arise from leaf axils. Freely flowering; more than 25 open flowers per lateral branch and more than 150 open flowers per plant. Flowering continuously for at least seven weeks. Flowers persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about ten to twelve weeks are required. Actual time to flower is primarily dependent upon temperature and light intensity.

*Post-production longevity.*—Excellent post-production longevity; plants maintain good foliage and flower substance for about 51 days under interior environmental conditions. Individual flowers last about 26 days on the plant.

*Flower diameter.*—About 2.4 cm.

*Flower height.*—About 1.5 cm.

*Flower buds.*—Shape: Initially oblong, becoming tubular ovoid with development. Length: About 1.3 cm. Width: About 6 mm. Color: Initially, 138C, then 63D with development.

*Petals.*—Quantity: About 24 to 28 per flower arranged in three to five rows. Length: About 5 mm to 6.5 mm. Width: About 5 mm to 6 mm. Aspect: Flat to slightly upright. Shape: Ovate. Apex: Obtuse. Margin: Entire. Texture, upper and lower surfaces: Glabrous, smooth. Color: When opening, upper surface: 57B. When opening, lower surface: 69C. Fully opened, upper surface: 57B; color becoming closer to 57C with development. Fully opened, lower surface: 69B.

*Sepals.*—Quantity: Four fused at base. Length: About 4 mm. Width: About 1.5 mm. Aspect: Erect. Shape: Oblong. Apex: Acute. Base: Obtuse. Margin: Entire. Texture, upper and lower surfaces: Glabrous, smooth. Color, upper and lower surfaces: 138D.

*Peduncles.*—Length: About 3 mm to 8 mm. Diameter: About 2 mm. Aspect: Erect. Strength: Strong, rigid. Texture: Smooth, glabrous. Color: 138C.

*Reproductive organs.*—Stamens: Quantity per flower: Eight. Anther shape: Elliptic; flat. Anther size: About 0.3 mm. Anther color: Close to 150D. Pollen amount: Scarce. Pollen color: Close to 12A. Pistils: Quantity per flower: Four. Style length: About 1 mm. Style color: 138D. Stigma shape: Flat, rounded. Stigma color: 8D. Ovary color: 138D. Seed: Quantity produced per plant: About 500. Length: About 0.1 mm. Diameter: About 0.05 mm. Color: Close to 166C.

Disease/pest resistance: Plants of the new *Kalanchoe* have not been observed to be resistant to pathogens and pests common to *Kalanchoes.*

Temperature tolerance: Plants of the new *Kalanchoe* have been observed to tolerate low temperatures of 16° C. and high temperatures of 35° C.

Garden performance: Plants of the new *Kalanchoe* have been observed to perform well in the garden and are tolerant to rain and wind.

It is claimed:

1. A new and distinct cultivar of *Kalanchoe* plant named 'Cher', as illustrated and described.

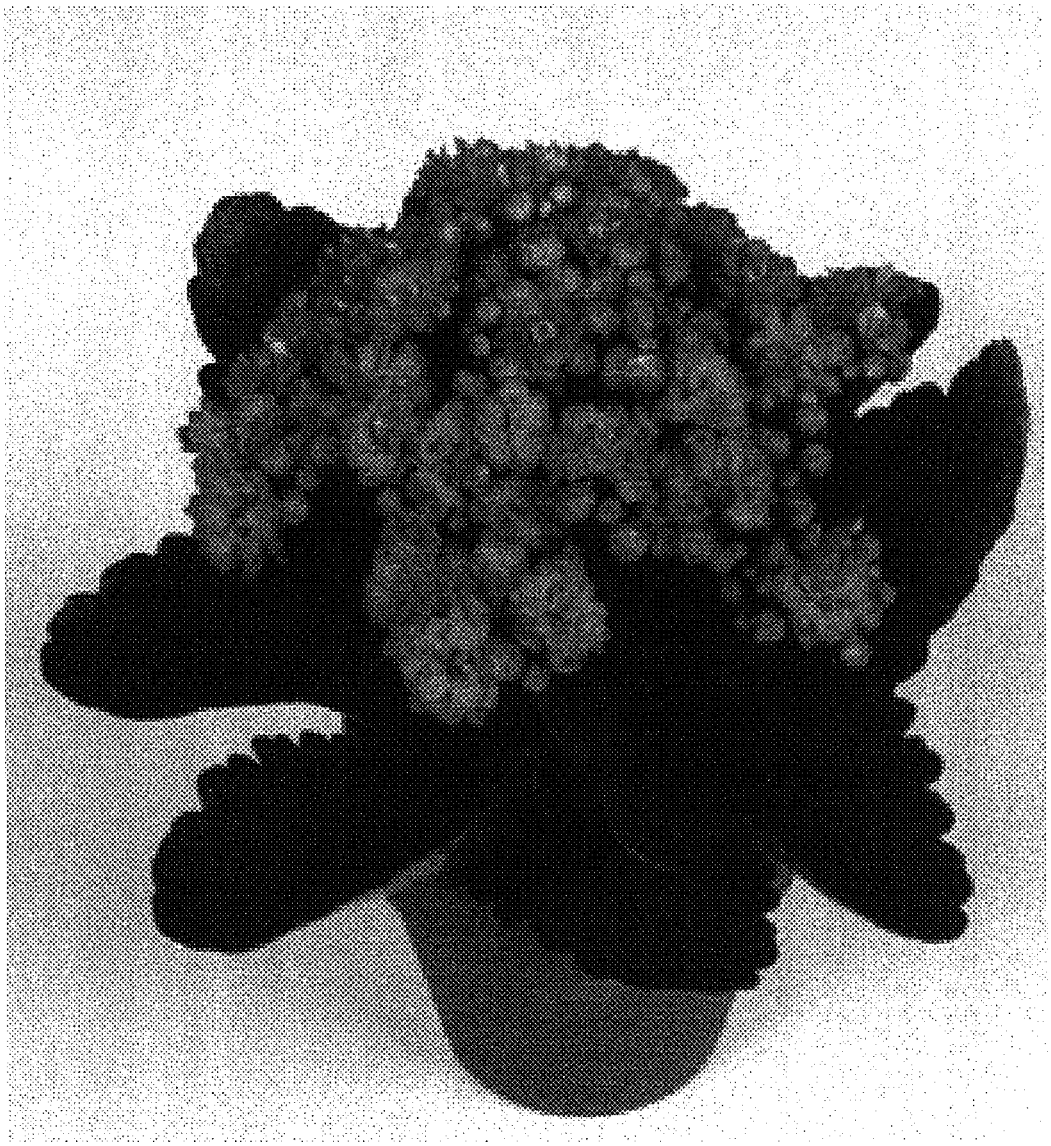

* * * * *